US00PP37300P2

(12) United States Plant Patent
Murray, Jr.

(10) Patent No.: US PP37,300 P2
(45) Date of Patent: Mar. 3, 2026

(54) HOP PLANT NAMED 'Greenmont Mother'

(50) Latin Name: *Humulus lupulus L.*
Varietal Denomination: Greenmont Mother

(71) Applicant: Greenmont Mother Patent LLC, Charlottesviile, VA (US)

(72) Inventor: James B. Murray, Jr., Charlottesville, VA (US)

(73) Assignee: GREENMONT MOTHER PATENT LLC, Charlottesville, VA (US)

( * ) Notice: Subject to any disclaimer, the term of this patent is extended or adjusted under 35 U.S.C. 154(b) by 0 days.

(21) Appl. No.: 19/003,159

(22) Filed: Dec. 27, 2024

(51) Int. Cl.
*A01H 5/02* (2018.01)
*A01H 6/28* (2018.01)

(52) U.S. Cl.
USPC ..... Plt./236

(58) Field of Classification Search
USPC ..... Plt./236
See application file for complete search history.

(56) References Cited

U.S. PATENT DOCUMENTS

| | | | |
|---|---|---|---|
| PP35,570 | P2 | 1/2024 | Sattler |
| PP35,580 | P2 | 1/2024 | Townsend |
| 2023/0210036 | P1 | 6/2023 | Kuji et al. |
| 2023/0292641 | P1 | 9/2023 | Kuji et al. |
| 2023/0309429 | P1 | 9/2023 | Perrault et al. |
| 2024/0147880 | P1 | 5/2024 | Matthews et al. |

OTHER PUBLICATIONS https://news.virginia.edu/content/discovery-wild-hops-brews-new-possibilities-virginia-farm. Retrieved from the Internet on Mar. 19, 2025.*

Havill, Joshua S., et al. "Registration of seven powdery mildew-resistant wild hop germplasm lines." Journal of Plant Registrations 17.1 (2023): 171-179.

Kenny, "Identification of U.S. Grown Hop Cultivars by Hop Acid and Essential Oil Analyses," J. Amer. Soc. Brewing Chemists 48(1):3-8, 1990.).

Peacock, et al. "Varietal Identification of Hops and Hop Pellets," Master Brewer Assoc. of the Americas Technical Quarterly 27:81-85, 1992.

Rassem, Hesham HA, et . . . al. "Techniques for extraction of essential oils from plants: a review." Australian Journal of Basic and Applied Sciences 10.16 (2016): 117-127.

* cited by examiner

*Primary Examiner* — Susan Mccormick Ewoldt
(74) *Attorney, Agent, or Firm* — Barnes & Thornburg LLP

(57) ABSTRACT

'Greenmont Mother' is a strong, robust hop plant, light yellowish green in color with smaller leaves in comparison to other hops and reaches the full height of over 18 feet (5.5 meters) commercial hop trellis with moderate foliage and long sidearms, with cones, that once fully matured, measure 1.5 inches-2.0 inches (3.81 cm to 5.08 cm), are abundant on the bine, and have an herbal and citrus, tea-like aroma, with low alpha and beta acidity.

11 Drawing Sheets

Figure 1:
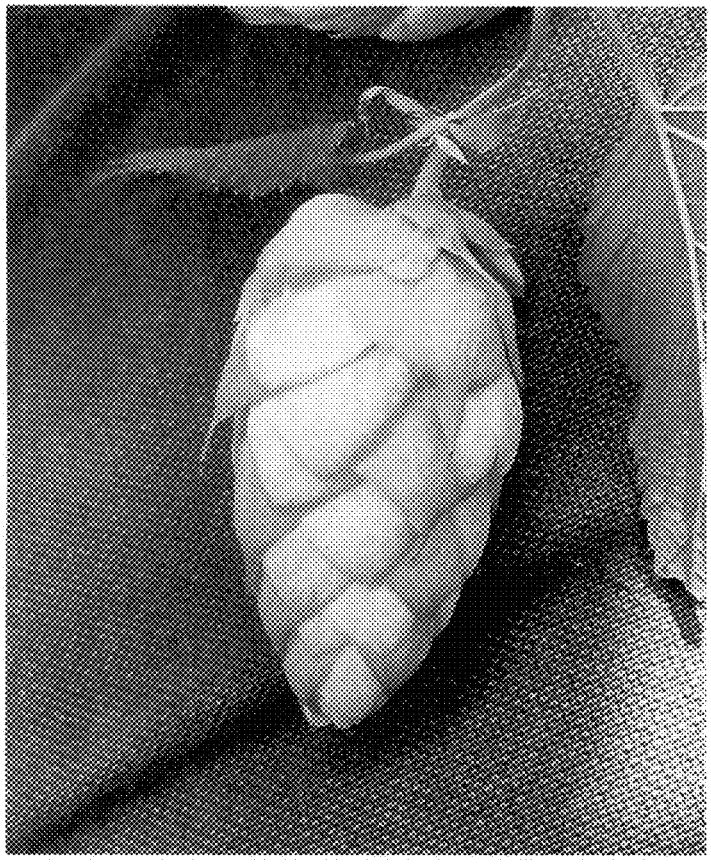

Genus and species:
Latin name: *Humulus lupulus* L.
Variety denomination:
Varietal denomination: 'Greenmont Mother'.

BACKGROUND OF THE NEW PLANT

The present disclosure describes a new and distinct hop variety, botanically known as *Humulus lupulus* L. and hereinafter referred to by the variety name 'Greenmont Mother'. 'Greenmont Mother' is a selection from a controlled cross of the hop female parent 'Stony Point' (not patented) and the male parent 'Greenmont Male Wild' (not patented).

A main vine ("bine") consists of a single flexible cylinder that produces pairs of leaves at nodes separated by variable distances along the length of the bine. The length of main bine between a pair of nodes is known as an internode. A bud is produced in the junction between leaf and bine, which junction is also known by the botanical term axil. Such a botanical term, as well as other botanical terms herein, are generally known to those of skill in the art and can also be found in standard botanical texts such as Simon, E. W., et al., Lawson's Textbook of Botany—Revised, University Tutorial Press Ltd., London, England, 14th Ed. 1966. The bud grows and develops into a lateral, also known as a side-shoot or side-arm, with the same basic vegetative structure as the main bine. The buds on the laterals develop into groups of flowers that later mature into cones (strobiles). Because the laterals produce and support the cones of the hop, the structure of the laterals strongly influences the number of cones produced and hence the ultimate commercial yield of a variety.

The cones are the useful brewing commodity and are referred to as "hops" in the commercial industry. Each cone is a group of flowers (inflorescence) consisting of sepals and petals (bracts and bracteoles) mounted on a central strig (or rachis). The resultant structure resembles a small pinecone or fir cone but is non-woody and green in color. In nature, the bracteoles support the seed of the plant. Hops contribute towards the bitterness and aroma in beer as well as foam quality, flavor, and taste stability. Various hop varieties have various special uses in the beer brewing industry. Aroma hops are used to impart flavors by virtue of the distinct profiles of their essential oils and terpene alcohols, among other compounds, as well as to supply bitter flavors based on specific contents of bitter acids, namely, terpenophenolics, mostly humulones. Examples of aroma hops are the cultivars known as variety 'Willamette' (non-patented), variety 'Centennial' (non-patented), variety 'Sterling' non-patented), variety 'Cascade' (non-patented), and variety 'Glacier' (non-patented). Many aroma varieties are susceptible to fungal pathogens, in particular powdery mildew, and otherwise exhibit less than ideal agronomic traits.

Complete descriptions of the botanical structure of the hop plant are given in Burgess, "Hops—Botany, Cultivation and Utilization," Weed Crop Series, Interscience Publishers, Inc., New York, 1964 and Neve, "Hops," von Nostrand Reinhold, New York, 1991.

A trellis of poles and wire, commonly 18 feet (5.4864 meters) height and known as a "high trellis," supports strings that the main bines climb. The main bines grow to the top of the trellis, where they produce the laterals that support the groups of flowers that develop into the cones. Typically, the laterals bear cones only in the upper parts of the plant (i.e., closer to the main bine); the distance from the main bine varies from one variety to another. When the cones are physiologically mature (ripe), the cones are harvested, then dried and compressed into bales for market, where the cones are typically used for the production of beverages such as beers, ales and related alcohol-containing liquids.

Different varieties of hops have differences in the chemical constituents of the lupulin of their cones. Accordingly, chemical analysis of such differences can be useful in distinguishing one hop variety from another. Such analysis is generally performed by high pressure liquid chromatography ("HPLC") of the soft resins along with gas liquid chromatography ("GLC") of the essential oils. Recently, Kenny developed a key for differentiation of hop varieties based on chemical analysis of the soft resins. (Kenny, "Identification of U.S. Grown Hop Cultivars by Hop Acid and Essential Oil Analyses," J. Amer. Soc. Brewing Chemists 48(1): 3-8, 1990.) Further, Peacock and McCarty, as well as Kenny, have developed keys for the differentiation of hop varieties based on chemical analysis of the essential oils. (Peacock and McCarty, "Varietal Identification of Hops and Hop Pellets," Master Brewer Assoc. of the Americas Technical Quarterly 27:81-85, 1992; Kenny, supra.) These keys are based on gross differences in the amounts of, and ratios between, major constituents, which differences are large enough to overcome variation inherent in the analytical analysis of biological material.

SUMMARY

The following are the outstanding and distinguishing characteristics of this new variety when grown under normal horticultural practices in Keene, Virginia (VA).

Figure 2:
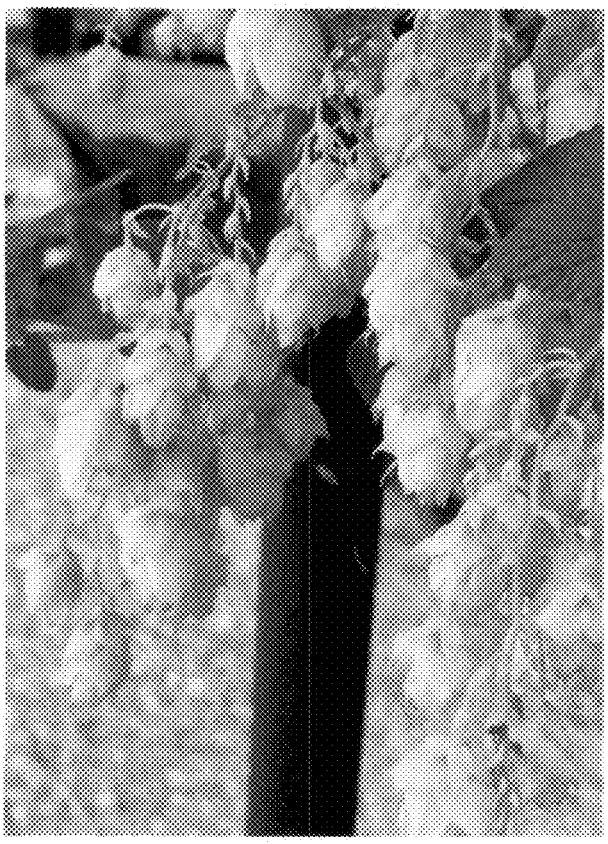
Figure 3:
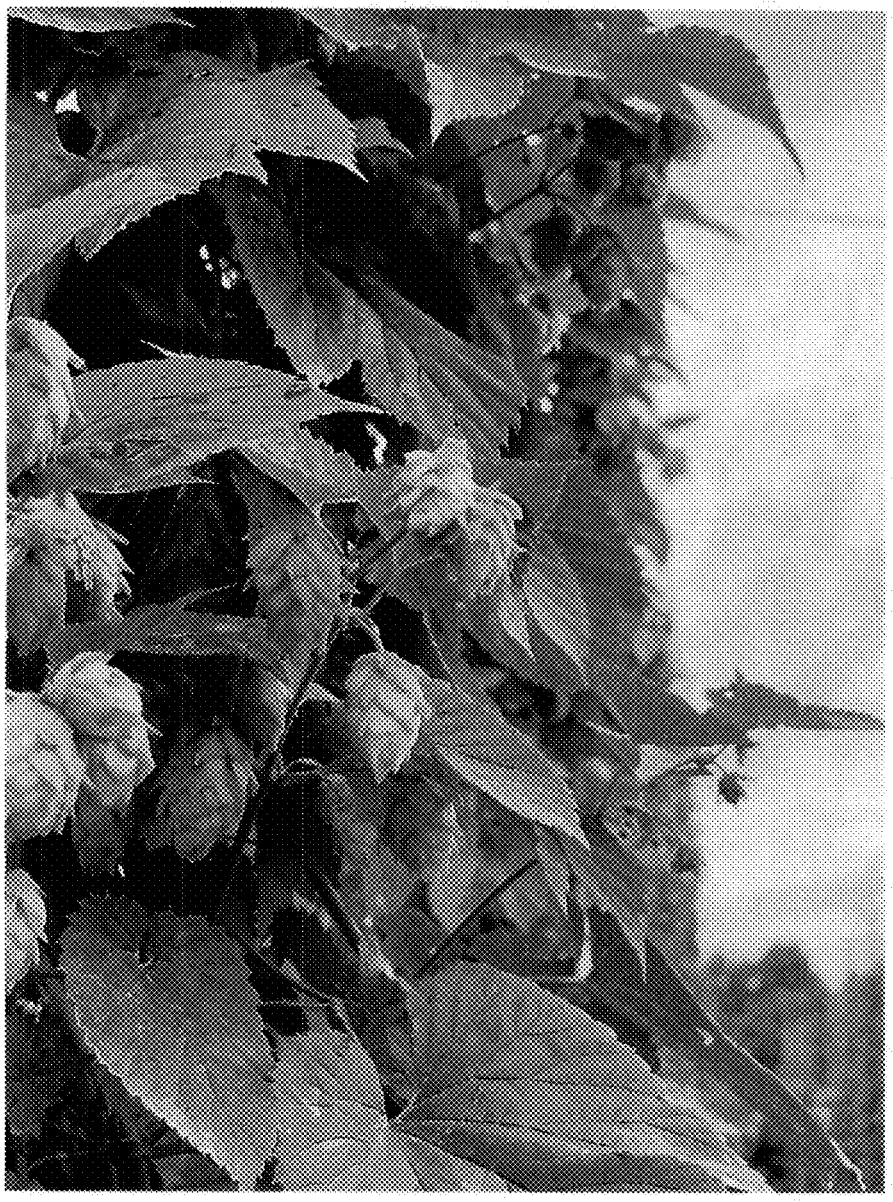

The hop plant described and claimed herein is illustrated by the accompanying photographs which show the plant's overall plant shape, leaf shape and cone shape. FIGS. 1, 2 and 3 are of a five-year-old plant and parts thereof, grown in Keene, Virginia, USA in August 2023 while FIG. 6 is also of a five-year-old plant grown in Keene, Virginia, USA taken in June 2023. FIG. 7 is of a six-year-old plant in July 2024, grown in Keene, Virginia. The colors shown are as true as can be reasonably obtained by conventional photographic procedures.

The present disclosure provides a new variety of hop (*Humulus lupulus* L.), which has been named 'Greenmont Mother'. The new variety comprises the 'Greenmont Mother' hop plant which is distinguished from other varieties of hop plant by its smaller and lighter-colored leaves, lower relative alpha and beta acidity and aromatic properties. Greenmont Mother is particularly suited for the production of beverages such as beers, ales and related alcohol-containing liquids.

BRIEF DESCRIPTION OF THE PHOTOGRAPHS

This new hop plant is illustrated by the accompanying photographs which show the plant and leaves. The colors shown are as true as can be reasonably obtained by conventional photographic procedures. The photographs are of plants that are 2-4-year-old plants.

FIG. 1. Shows the mature cone and lower surface of a leaf of the 'Greenmont Mother' hop plant.

FIG. 2. Shows the immature cone bunch of the 'Greenmont Mother' hop plant.

FIG. 3. Shows the mature cones of a 'Chinook' hop plant, to be compared to FIG. 5

Figure 4:
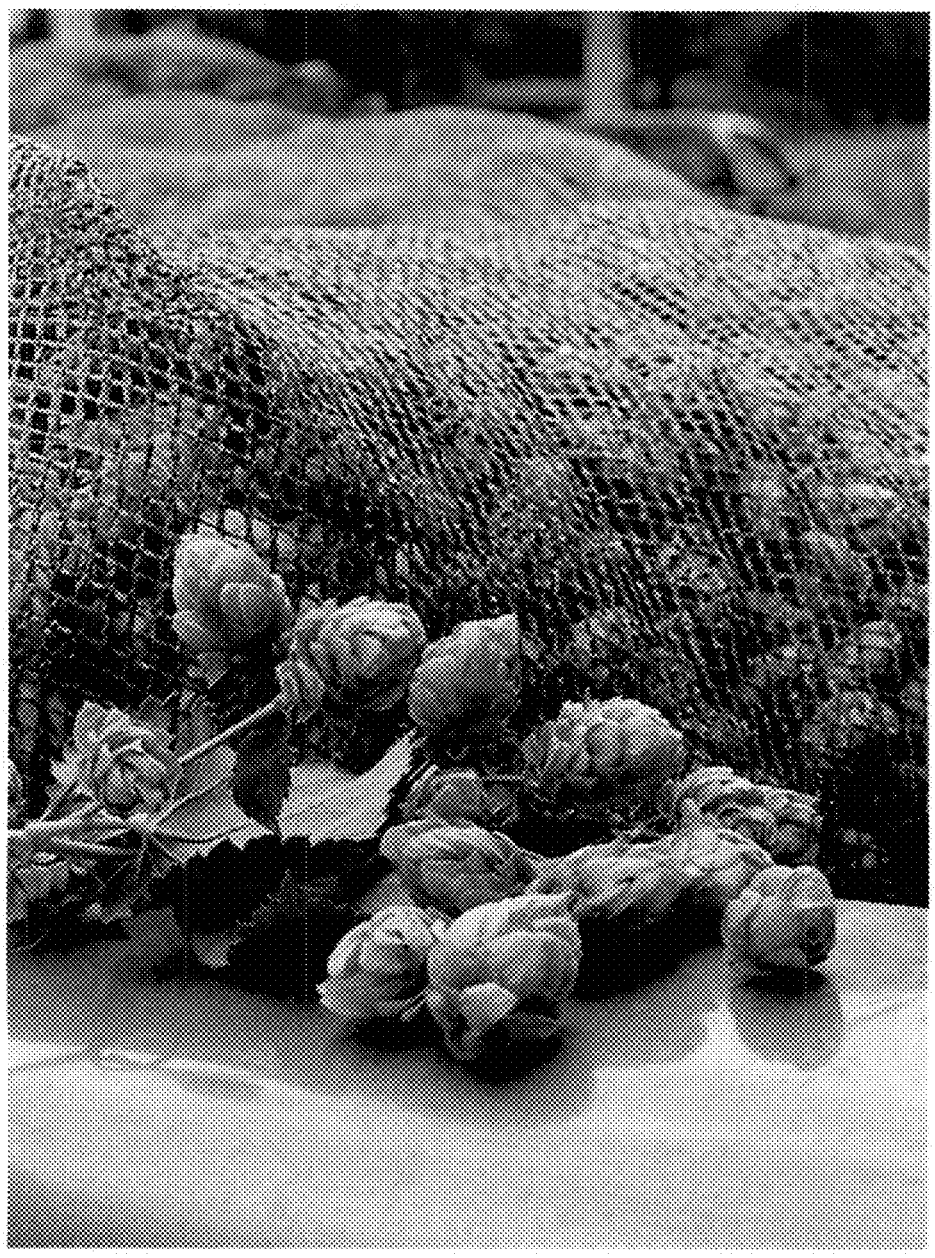

FIG. 4. Shows the mature cones of a 'Crystal' hop plant, to be compared to FIG. 5.

Figure 5:
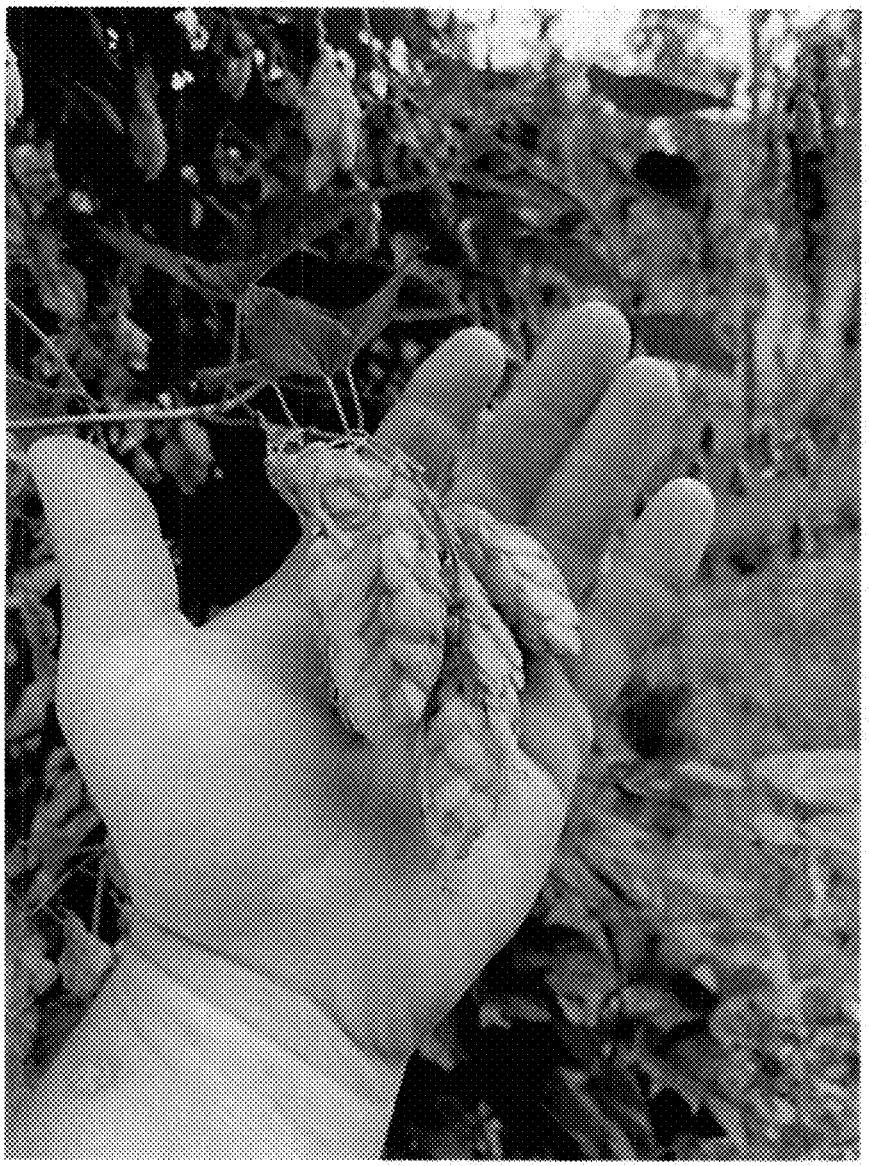

FIG. 5. Shows the mature cones of a 'Greenmont Mother' hop plant.

FIG. 6. Shows the Upper Surface of a leaf of the 'Greenmont Mother' hop plant.

FIG. 7. Shows a leaf of the 'Greenmont Mother' hop plant in comparison to the leaf of a 'Crystal' variety grown in the same field.

FIG. 8. Shows a Cluster of three cones of the 'Greenmont Mother' hop plant.

FIG. 9. Shows the immature cones of the 'Greenmont Mother' plant [not ready for harvest], July 2024, at the time other varieties in the same field are beginning harvest.

FIG. 10. Shows the Bine and Sidearms of the 'Greenmont Mother' hop plant, September 2024.

FIG. 11. Shows a Cluster of mature cones of the 'Greenmont Mother' hop plant.

DETAILED DESCRIPTION

The present disclosure provides a new variety of hop (*Humulus lupulus* L.), which has been named 'Greenmont Mother'. The new variety comprises the 'Greenmont Mother' hop plant and is distinguished from other varieties of hop plant by its smaller and lighter-colored leaves, a lower percentage of alpha-acids, powdery mildew resistance, downy mildew tolerance, which are significant improvements in agronomic traits, and a distinctly herbal/tea-like aroma.

The following detailed description of the 'Greenmont Mother' cultivar is based on observations of various 2-4-year-old plants, first propagation generation, growing on a hop farm in Keene, Virginia, USA between 2017 and 2018. The new variety of hops has been asexually propagated by vegetative cuttings or rhizomes. and the distinctive characteristics of the new variety have proven to be stable and are reproduced true-to-type in successive generations. The original 'Greenmont Male Wild' plant has been observed growing in an area near Keene, Virginia, USA.

Parentage: The new cultivar was cultivated by a parental cross between the parent mother 'Stony Point' and parental father 'Greenmont Male Wild', through propagation, or selective breeding.

*Female parent.—Humulus lupulus* 'Stony Point' (varietal name).

*Male parent.*—*Humulus lupulus* 'Greenmont Male Wild' (varietal name).

The new cultivar has not been evaluated under all possible environmental conditions but was grown and developed for Keene, Virginia, USA, (USDA hardiness zone 7A, approximate GPS Coordinates: 37° 53'15.6"N 78° 34'55.5"W). Certain characteristics of this cultivar such as growth, color, and cone chemical composition may vary with different grower practices and changing environmental conditions (e.g., light, temperature, moisture, nutrient availability, or other factors).

'Greenmont Mother' has less compact internodes than 'Stony Point' and has denser lupulin glands and a faster growth rate than 'Greenmont Male Wild'.

The associated botanical description below is based on observations made of the varietal in Keene, VA in May, June, July, August, September and October of 2017, 2018, 2019, 2020, 2021, 2022, 2023, and 2024. All colors are described according to the 4$^{th}$ edition of The Royal Horticultural Society (R.H.S.) Colour Chart. Certain characteristics and descriptions may vary somewhat depending on cultural and environmental conditions and could vary season to season. Quantified measurements are expressed as an average of measurements taken from individual sample plants. Measurements of any individual or group of plants of the new variety may vary from the stated measurements.

Classification:

*Family.*—Cannabaceae.

*Classification.*—*Humulus lupulus* L.

*Common name.*—Hop.

Asexual propagation:

*Type.*—Vegetative cuttings or rhizomes.

Plant description:

*Plant and growth habit.*—The variety's produce annual climbing bines that grow to a height of approximately 20 feet (6.096 meters). The variety does not currently self-pollinate. The plant growth type is normal, not dwarf.

*Plant shape.*—Cylindrical to club. The plant growth is generally fusiform but with additional lateral development towards the top of the plant compared to other varieties.

*Color.*—Fully developed (mature) Soft yellow green (RHS 140B) on main bine.

Lateral branch description:

*Bines.*—Growth characteristic — The variety's bines climb clockwise with the aid of trichomes on the bine.

*Bine.*—Color — Brilliant Yellowish Green (RHS 154C). The color of the bine is distinctly lighter than other varieties.

*Bine.*—Thickness — Bine thickness ranging from ¼" to ½" of an inch (0.635 cm to 1.27 cm) but may increase on more mature plants of this varietal.

*Laterals.*—Position — Laterals are evenly spaced along the main bine and grow from the auxiliary buds at nodes on the bine.

*Laterals.*—Growth Habit — The laterals produce inflorescence that branch off between 3-15 times to produce a cluster of hop flowers.

*Laterals.*—Length — Considered average compared to most commercial varieties. This variety produced lateral shoots at the head which may extend from 40 mm to 90 mm. Lower lateral side shoots may extend from 0 mm to 30 mm. Internodes — Length — 25 cm to 50 cm. There may be quantities of 20 to 35 internodes in a single bine.

*Stems.*—Generally — The stems of the variety are annual in nature and emerge from both the crown and rhizomes in May and grow along suitable supports.

*Dormancy.*—Generally — This variety remains dormant longer than other commercially available varieties like Cascade or Chinook. This variety emerged from dormancy at the Keene, VA location roughly two weeks later than Chinook and one week later than Crystal, Cascade and Newport.

*Shoot growth rate.*—Generally — Considered to be similar to other common commercial varieties but delayed due to longer dormancy. This variety can grow up to 6-9 meters in a single growing season. While other varieties grow longer shoots in May, this variety experienced greater growth in June.

*Bine stems.*—Shape — The stem is generally round to hexagonal.

*Bine color.*—Early Season: green, Late Season: brown. Bine begins bright green in color (approximately May & June of each spring), matching Brilliant Yellowish Green, RHS 154C. Bines turn brown as the plant matures (reaching brown bottom to top, all brown by the top in approximately mid-August each summer), matching RHS 146C. When it reaches 6 feet tall (1.8 meters), it gets woody. It's ready for harvest in mid-September most years.

*Lateral shoots.*—Size — Shoot bines are typically between ¼" and ½" an inch (0.635 cm to 1.27 cm) in diameter, the shoots can be 1 foot to 2.5 feet long (30 cm to 76.2 cm).

*Cultural measures.*—Generally — The 'Greenmont Mother' variety displays vigorous growth on an 18 foot tall (5.486 meters) trellis. Approximately, 45 of the 50 plants tested in a plant trial (2023) grew to the top of the trellis (18 feet) after 4-6 weeks of self-training in mid-May and reach the top of the wire of an 18-foot trellis around mid-June to early July. Final length of most bines reached closer to 20 feet, or 6.1 meters, extending horizontally down the trellis wire when it surpassed vertical support.

*Stipule growth direction.*—Generally — Downward.

*Plant shape.*—Generally — The plant growth is generally fusiform but with additional lateral development towards the top of the plant compared to varietals Crystal, Newport and Chinook.

Foliage description:

*Leaves.*—Generally — The leaves of this variety are born in pairs at each node on the main bine.

*Leaves.*—Arrangement — Opposite.

*Stipules.*—Location — Located at the petiole base.

*Stipules.*—Arrangement — N/A.

*Leaves.*—Size — Leaves are much smaller than other common varieties. Leaves do not become as broad as other commercially available varieties.

*Leaf.*—Width — Approximately 3-5 inches in width (7.62 cm to 12.7 cm).

*Leaf.*—Length — 1.5-2.5 cm.

*Leaf.*—Shape of Apex — acute to acuminate, tapers to a sharp point.

*Leaf.*—Shape of Base — cordate to truncate, base lobes are overlapping or rounded.

*Leaf.*—Shape — Palmate, with 3-5 divided palmate lobes.

*Leaf*.—Venation — palmate, 3 to 5 primary veins radiating from the base with secondary veins branching off of the primary veins. Midrib and veins are prominent, especially on the underside of the leaf. Veins are green to pale green (RHS 141D) in adult plants. Juvenile veins can be reddish or purplish (RHS 58A), especially near the petiole or midrib.

*Leaf margin*.—Highly serrated and dentate.

*Sinus*.—Clefts — Shape — More Deeply Cut than most varieties.

*Leaf color*.—Upper surface — Strong Yellowish Green (RHS 143C).

*Leaf color*.—Lower surface — Light/Moderate Yellowish Green (RHS 139D).

*Leaf petiole*.—Color — Light Reddish Brown (RHS 177B), but the lower half is dull yellow (RHS 149A).

*Leaf petiole*.—Position — Connects to the leaf at the center line. Slightly curved to the main bine/lateral arm. Connects at nearly a right angle to the main bine/lateral arm. Petiole connects into a hastate cleft in the base of the leaf.

*Leaf petioles*.—Shape: Petiole is slightly curved and cylindrical with a two year mean petiole diameter of 5.0 mm, and ranging between 3.5 mm to 6 mm.

*Leaf petiole*.—Length: Two-year-mean petiole length is 6.5 cm, and ranging between 5 cm to 8 cm.

*Leaves*.—Upper Surface Texture: The surface of the leaf is more delicate than 'Chinook' and 'Centennial' varietal's leaves. Serration makes the outer edge of the leaf stiffer than compared to 'Chinook' and 'Centennial' varietals.

*Leaves*.—Lower Surface Texture: The bottom surface of the leaf has a substantial number of trichomes that give it a much rougher sandpaper-like texture.

*Surface characteristics*.—Upper surface of the leaf is smooth. Underside of the leaf is rougher and lighter in color than the upper surface. All vascularity is located on the underside of the leaf.

Flower description:

Flower arrangement and habit:

*Generally*.—Typically, cones are found in high number clusters borne at nodes on a lateral that are close to the main bine ("basal lateral nodes"). Progressively fewer cones are found in the clusters located at nodes progressively farther away from the main bine. Ultimately, the lateral terminates in a tip bearing a single cone. 'Greenmont Mother' yields a low number of cones at the basal lateral nodes as well as at nodes located farther away from the main bine. (FIG. 2.) The basal lateral nodes of 'Greenmont Mother' have produced up to 15 cones. Conventional low yielding hop varieties typically bear clusters of about 8-16 cones at basal lateral nodes, while conventional high yielding varieties typically bear clusters of about 16-28 cones at basal lateral nodes. Cones begin to form in late August and begin to mature in mid-September under the conditions prevailing in Central Virginia. As the cones mature, they grow from small loosely-packed flowers to larger tightly-packed ovoid cones. Total number of cones of side shoot from middle of plant (2-year mean: 40 cones/branch, ranging from 10 to 50); total number of cones of side shoot from upper third of plant (2-year mean: 30 cones/branch ranging between 10 to 50); number of cones per node of side shoot of plant (2-year mean: 8 cones/node, ranging between 6 to 10).

*Time of flowering*.—July 12 to July 18.

*Time of picking maturity of cones*.—Mid-September to early October.

Inflorescence buds:

*Description*.—Two-year-mean 100-cone-weight is 28 g in dry matter.

*Length*.—Medium (2-year mean: 8.25 cm, ranging between 5 cm to 11.5 cm).

*Diameter*.—2-year mean: 3.5 cm, ranging between 2.5 cm to 4.5 cm.

*Shape*.—Narrow ovoid.

Spike bracts:

*Length*.—Slightly large (2-year mean: 2.05 cm, ranging between 1.8 cm to 2.3 cm).

*Width*.—Two-year-mean bract width is 1.05 cm, ranging between 0.8 cm to 1.3 cm.

*Shape*.—The width/length ratio is medium (two-year-mean width/length ratio of bracts is 0.7, ranging between 0.5 to 0.9).

*Apex*.—The length of apex of bract is slightly short.

*Degree of opening of bracts*.—Closed.

*Color of cone*.—Slightly yellow green, (RHS color 140B).

*Margin*.—Entire.

Bracteoles:

*Length*.—Two-year-mean length of bracteoles is 1.25 cm, ranging between 1.0 cm to 1.5 cm.

*Width (cm)*.—Two-year-mean width of bracteoles is 0.75 cm, ranging between.5 cm to 1.0 cm).

*Shape*.—Ovate.

*Apex*.—Round.

*Margin*.—Entire.

*Color*.—Strong yellowish green. (RHS color 149C).

Pedicels: Present, see FIG. 1. Average length of pedicel: 1.4-2.5 cm.

Average diameter of pedicel.—1.3-1.5 mm.

*Average color of pedicel*.—RHS 142A (when immature), RHS 141D (when mature).

Reproductive organs:

*Stamens*.—Not observed.

*Pistils*.—Not observed.

Disease resistance: Resistant to downy mildew (*Pseudoperonospora humuli*) and tolerant to powdery mildew (*Podosphaera macularis*). See Exhibit A behind the images for further details of mildew and pest resistance and tolerance.

EXAMPLE

Use of Fungicides and Pesticides

In the 2024 growing season, we did not spray for pests or fungus on 'Greenmont Mother'. That is the only variety that didn't require intervention. All of the other hop varieties we grow—'Crystal', 'Cascade', 'Chinook' and 'Newport'—had to be sprayed with fungicides every 7-10 days.

We begin applying fungicide in early March each year, including 2024. The first application is a drench application through drip irrigation to target the roots, then we use aerial spray maintaining the 7-10 day schedule until one month before harvest.

Pesticides are applied through aerial spray as needed, with the guideline that pest colonization numbers need to meet a threshold before it is viable to spray. We stop spraying pesticides a month before harvest.

Harvest dates vary based on variety, beginning as early as the first week of July through the last week of August. 'Greenmont Mother' does not harvest until September.

'Greenmont Mother' has the unique capability to suppress the infection of downy and powdery mildew in comparison to other varieties. Cultivated varieties like 'Cascade' and 'Chinook' that show visible stunted growth require scheduled fungicide applications in order to suppress the infection while no fungicide is required for 'Greenmont Mother'. Other varieties that are infected may flare due to environmental conditions. Observations throughout the years determined that 'Greenmont Mother' has more adaptability to the environment than other varieties cultivated in the same conditions.

Below are the products and quantities used on our 'Crystal', 'Cascade', 'Chinook' and 'Newport' hop varieties grown in the same fields as 'Greenmont Mother'.

Fungicides:

Tanos—(Famoxadone 25% Cymoxanil 25%) at 8 oz/acre.

Kocide 3000—(Copper Hydroxide 46.1%) at 1 lb/acre.

Curzate 60DF—(Cymoxanil 60%) at 3.5 oz/acre.

Zampro—(Ametoctradin 26.9% and Dimethomorph 20.2%) at 12 oz/acre.

Pesticides:

Carbaryl 4L—(Carbaryl 42.6%) at 0.75 oz/acre.

Dipel ES—(Bacillus thuringiensis kurstaki (Btk) 23.7%) at 2 pints/acre.

Need oil—70% at 0.75 quarts/acre.

'Greenmont Mother' required no fungicides or pesticides, only irrigation. This is typical for the variety.

Form: The variety develops cones in clusters of as many as 15 cones. The cones develop relatively evenly along the length of the plant and sidearms with larger clusters located towards the end of the sidearms.

Strig:

*Generally*.—The strig is considered to be narrower than average commercial varieties.

Aroma: Due to their chemical characteristics, some hop varieties are referred to as aromatic, or low alpha hops, and are known to contribute good hop flavor and aroma. Other hop varieties are high in bittering potential (i.e., high in alpha acids) and are referred to as bitter or high alpha hops. 'Greenmont Mother' may be referred to as an aromatic or low alpha hop. Hop varieties in an intermediate varietal classification have medium levels of alpha acids and are referred to as dual-purpose hops. The aroma is moderate and very pleasant. Aroma *Citrus* x *paradisi* (grapefruit) with a hint of *Prunus* (peach) and herbal than most commercial varieties.

*Cone length*.—Cone length varies from 0.5 inches (1.27 cm) less mature plants up to 2 inches (5.08 cm) more mature plants when grown in Central Virginia ecological conditions.

*Cone tip*.—Shape — Ranging from blunt to a blunt point.

*Cone shape*.—Ovoid.

*Compactness*.—Ranging from compact in more mature plants to semi dense in younger plants.

*Bract tip*.—Shape — Ranging from cuspidate to the top of the cone to round at the bottom of the cone.

*Bracteole*.—Shape — N/A.

*Central rachis*.—Form — N/A.

*Lupulin glands*.—Numbers — The cones contain a range of 20 to 27 lupulin glands based on the maturity of the plant. Additionally, numbers of lupulin glands present will vary greatly year-to-year based on a multitude of external, environmental and cultural factors. Generally, the variety has a moderate to low number of glands compared to other varieties because of the lower-than-usual alpha acidity.

*Date of maturity*.—Mid-September to early October.

*Harvestability*.—Generally — The cones of mature plants are very harvestable.

*Bract tip position*.—The bract tip position is considered appressed at maturity.

*Yield per acre*.—Not Established.

*Cone bracteole*.—Color — N/A.

*Cone bract*.—Color — N/A.

Soft Resin Characteristics

Table 1 lists the total amount of alpha and beta acids, the ratio of alpha acids to beta acids, and estimates of the relative proportions of cohumulone and colupulone for 'Greenmont Mother'. This data was determined by HPLC analysis according to standard methods well known to those having skill in the art. (See, e.g., American Society of Brewing Chemists, "Hops Method 12: Analysis of Hops, Hop Powders and Hop Pellets by High Pressure Liquid Chromatography," in "Methods of Analysis," The Society, St. Paul, Mn., 8th ed. 1991.) Toluene extraction for total oil and hops storage index using methods known in the art. The data are expressed as ranging to account for inherent biological variation from sample to sample. Generally—the data provided here is based on the cones having a moisture content of between 10 and 12%.

Detailed analysis of the essential oils allows a further differentiation of 'Greenmont Mother' from other hops. Table 2 further distinguishes some of the varieties discussed.

Extraction and analysis of essential oils are performed illustratively using toluene extraction according to methods well known to those having skill in the art. (See for example, Hesham H. A. Rassem, Abdurahman H. Nour, Rosli M. Yunus., Techniques For Extraction of Essential Oils From Plants: A Review. Aust. J. Basic & Appl. Sci., 10(16): 117-127, 2016.) Preferably the essential oils are extracted by steam distilling previously dried hops for about four hours (with the steam of the distillation condensed using a cold-finger condenser). The resultant essential oils are then examined by Gas Liquid Chromatography (GLC) analysis.

TABLE 1

Profile
PROFILE

| Parameter | 'Greenmont Mother' |
|---|---|
| Alpha-acids (% w/w) | 2.68 |
| Beta-acids (% w/w) | 2.86 |
| Alpha/Beta Ratio (% w/w) | 0.94 |
| Cohumulone (% of alpha-acids) | 67.7 |
| Colupulone (% of beta-acids) | 81 |

TABLE 1-continued

| Profile PROFILE | |
|---|---|
| Parameter | 'Greenmont Mother' |
| Hops Storage Index (degradation of alpha and beta acids during storage and handling of the hops See : J. Am. Soc. Brew. Chem. 37 (4): 184-187.) | .022 |
| Total oil content (mLs/100 g) | 0.42 |
| Humulene (% of total oils) | 1.04 |
| Caryophyllene (% of total oils) | 5.11 |
| Farnesene (% of total oils) | 2.87 |
| Myrcene (% of total oils) - 50.63 | 50.63 |

Flavor of 'Greenmont Mother' is consistent with green or oolong teas and fruits such as persimmon.

Growth Characteristics

Although the early season growth rate and length of time for the hop bines to reach the top wire of a trellis vary widely due to factors such as climatic conditions and growth and harvest management, the early season growth of 'Greenmont Mother' is generally faster than other commercial varieties such as 'Cascade' and 'Chinook' and regularly climb to the top of an 18 foot (5.486 meters) trellis. Other common varieties do not exhibit the same heartiness of growth when cultivated in Central Virginia. 'Greenmont Mother' hop plants produce strong nodal sidearm growth in upwards of 24-36 inches (60.96 cm to 91.44 cm). 'Greenmont Mother' is a late-maturing hop.

Comparison with Parental Lines and Known Variety

'Greenmont Mother' is a distinct variety of hop. The 'Greenmont Mother' hop plant is distinguished from other varieties of hop plant by its smaller and lighter-colored leaves, lower relative alpha and beta acidity and aromatic properties.

The cones, once ready for harvest, are tightly packed and average 1.5 inches in length. The cones exhibit an aroma consistent with green or oolong teas and fruits such as persimmon. Picking dates for 'Greenmont Mother' hop plants are usually late September into early October. Yields per acre are currently unknown but early cultivation has shown stronger yields than several other commercially-available varietals.

'Greenmont Mother' is distinguished from the commercial hop variety 'Tettnang', 'Hallertau Mittelfreuh' and 'UK Golding' with differences between the four varieties described in Table 2:

TABLE 2

| Comparison with Similar Varieties Comparison with Similar Varieties | | | | |
|---|---|---|---|---|
| | 'Greenmont Mother' | ' Tettnang' | 'Hallertau Mittelfreuh' | 'UK Golding' |
| Aromatics | Green Tea, Persimmon | Spicy, Pepper, Black Tea | Floral, Citrus, Spicy | Citrus, Spicy |
| Maturity | Late | Early | Early | Mid Season |
| Alpha Acidity in cones | 2-3.5% | 3-6% | 3-5.5% | 4-5.5% |
| Beta Acidity in cones | 2.5-3.5% | 3-5% | 3.5-5.5% | 1.9-2.8% |
| Storage Stability | N/A | Good - 70% | Low - 55% | Good - 65-85% |

Genetic Testing

EXAMPLE

Methods

Genomic DNA was extracted from tissue samples. Sequencing libraries were prepared and sequenced on an Illumina NovaSeq S4 sequencing platform. Reads were mapped to the *Humulus lupulus* reference genome (drHumLupu1.1, NCBI RefSeq assembly GCF_963169125.1).1 using BWA-MEM.2 Variants were called with FreeBayes.3 Coverage statistics were calculated using samtools.4 MultiQC was used to summarize results.5

Sequencing Results

The table below shows sequencing results for *Humulus lupulus* L. 'Greenmont Mother'. After sequencing over 300 million sequencing reads, there were over 5 million distinct genetic differences, including over 150,000 insertions and deletions (indels) and over 5 million single nucleotide polymorphisms (SNPs).

TABLE 3

*Humulus lupulus* L. 'Greenmont Mother' sequencing results.

| Sample | Total Sequencing Reads | Coverage | Total Variants | SNPs | Indels |
|---|---|---|---|---|---|
| GMH _WA01 | 308,153,748 | 9.77X | 5,401,397 | 5,241,940 | 159,457 |
| GMH _WA02 | 311,164,184 | 9.75X | 5,401,301 | 5,241,556 | 159,745 |

CONCLUSIONS

In conclusion, the sequencing data presented in this report supports the identification of *Humulus lupulus* L. 'Greenmont Mother' as a genetically distinct hop variety. With over 300 million sequencing reads mapped to the *Humulus lupulus* reference genome, the high coverage and the large number of identified variants, including over 5 million SNPs and over 150,000 indels, provide compelling evidence of the unique genetic makeup of this variety. These genetic differences set 'Greenmont Mother' apart from other hop varieties, reinforcing its novelty and distinctiveness. As such, this unique genetic profile aligns with the criteria for plant patent protection, making 'Greenmont Mother' a strong candidate for patent eligibility based on its distinct and documented genetic characteristics.

What is claimed:

1. A new and distinct hop plant named 'Greenmont Mother' substantially as described and illustrated herein.

* * * * *

FIG.1 GREENMONT MOTHER cone

FIG. 2 GREENMONT MOTHER cone (immature)

FIG. 3 CHINOOK cones

FIG. 4 CRYSTAL cones

GREENMONT MOTHER cones

FIG. 6 GREENMONT LEAF
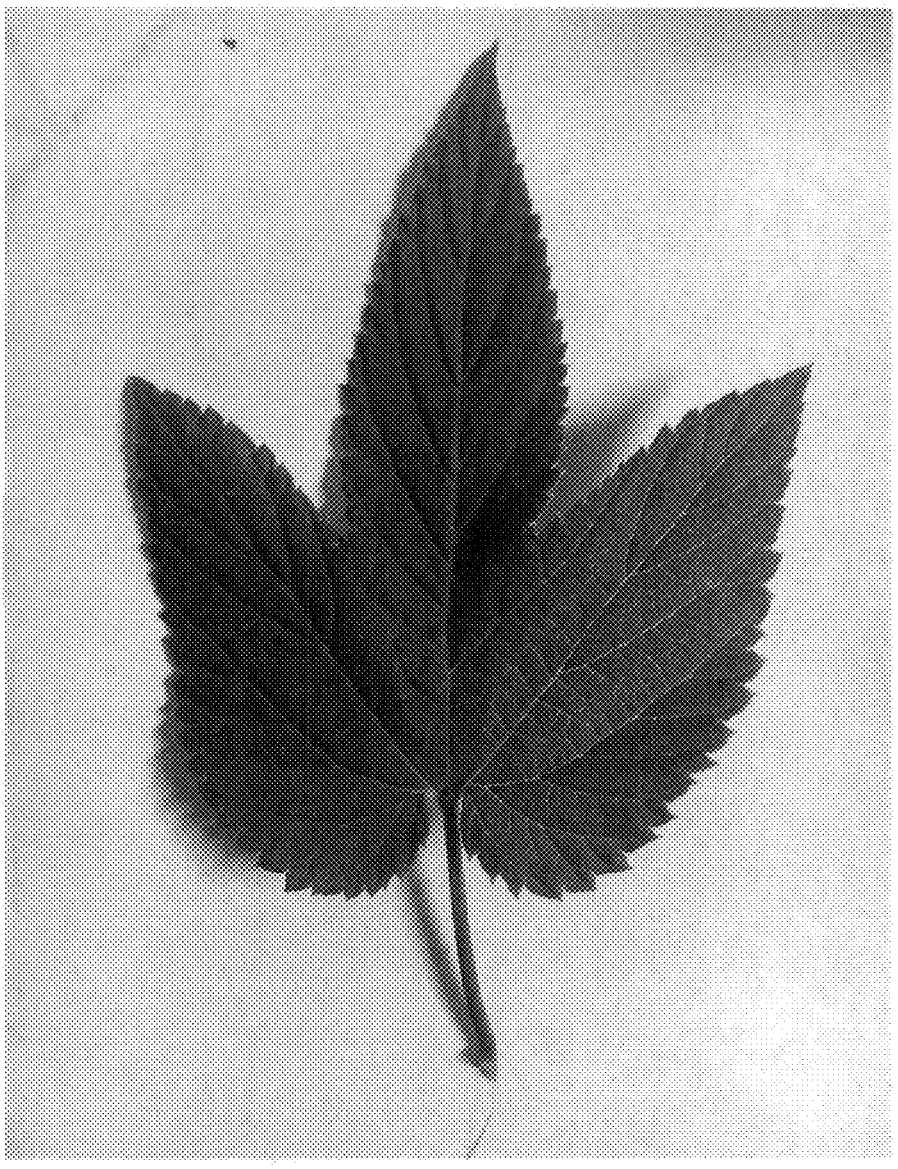

FIG. 7 GREENMONT leaf versus CRYSTAL leaf [smaller/top is Greenmont, larger/bottom is Crystal]
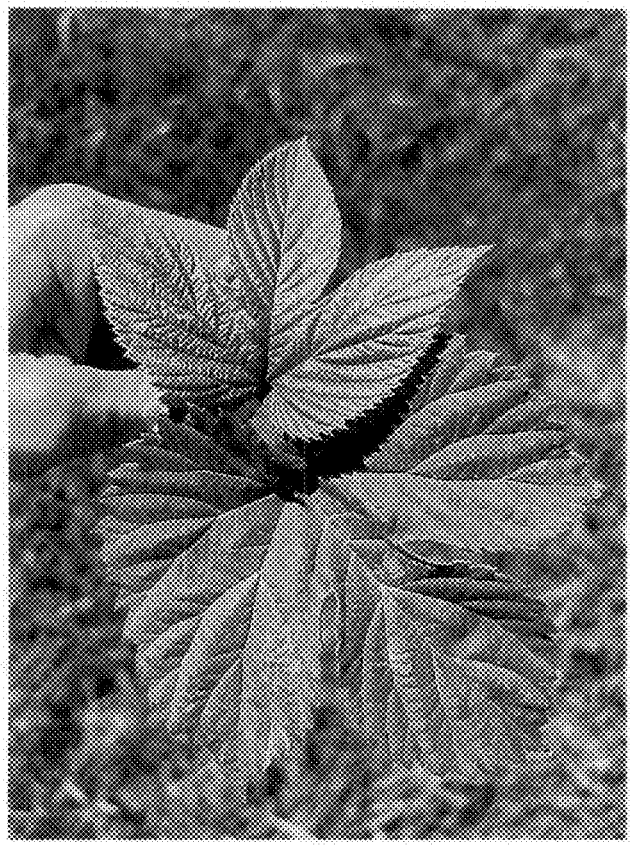

FIG. 8 GREENMONT cones on the bine
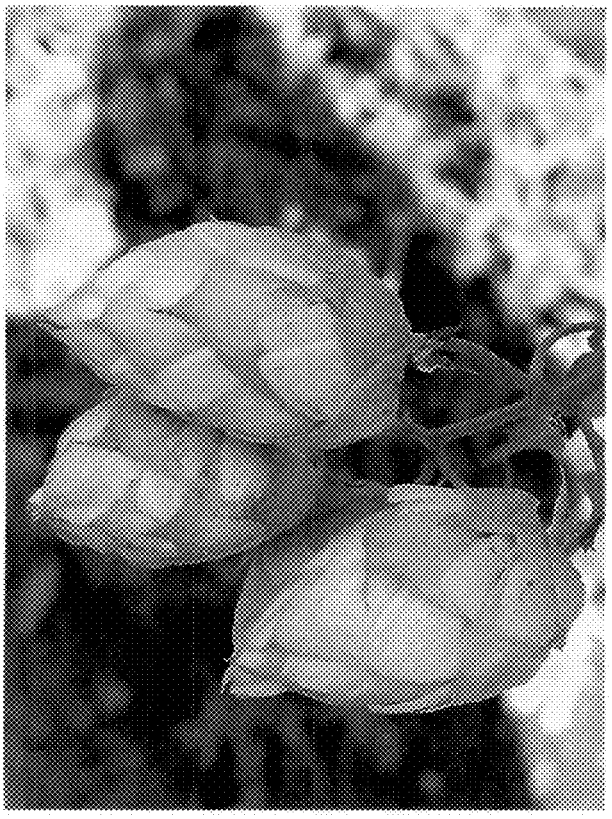

FIG. 9. GREENMONT MOTHER immature bine
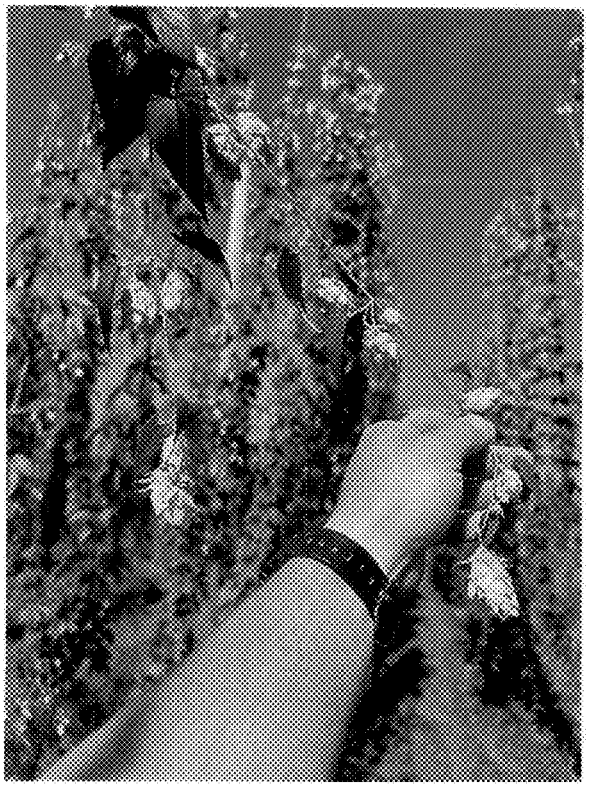

FIG. 10 GREENMONT MOTHER mature bine
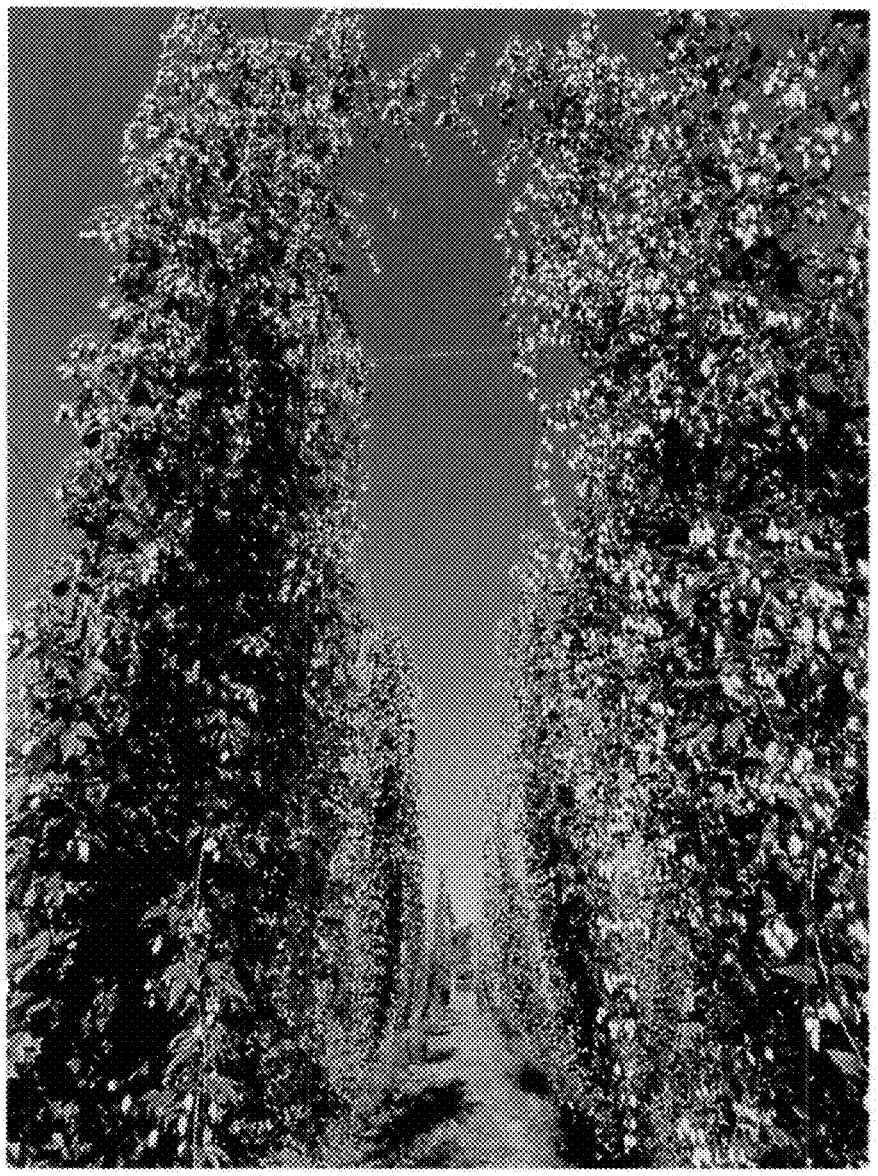

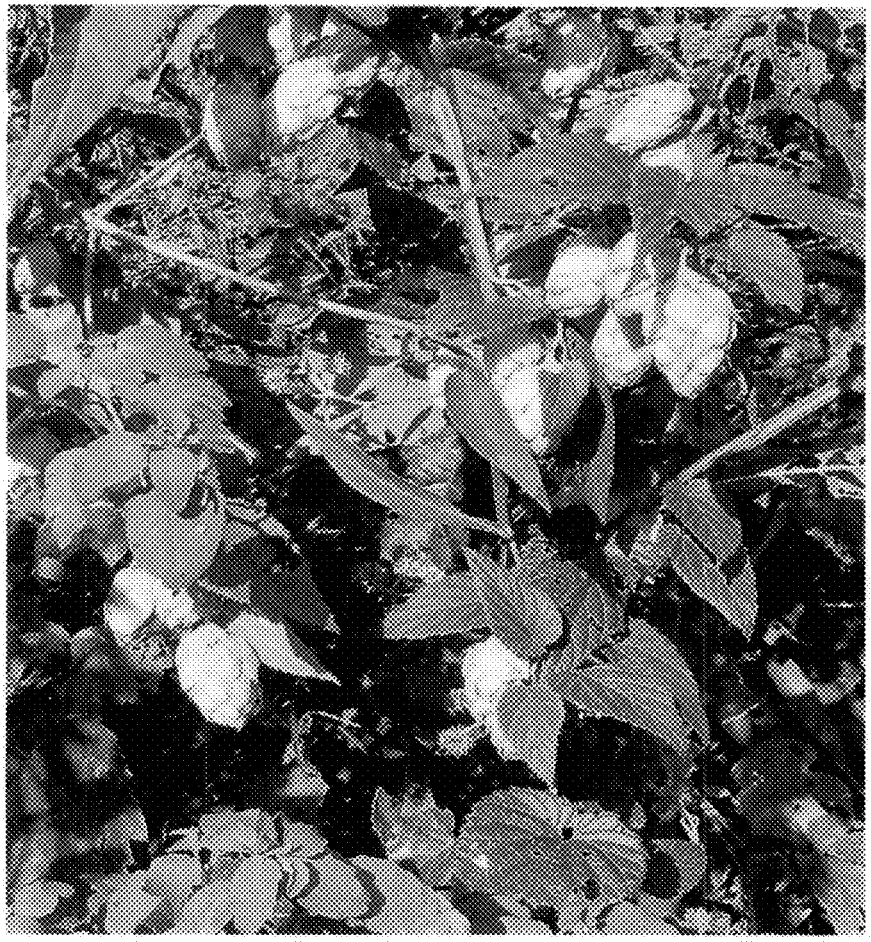

FIG. 11 GREENMONT MOTHER mature cones cluster